United States Patent [19]

Popovtzer et al.

[11] Patent Number: 4,997,824
[45] Date of Patent: Mar. 5, 1991

[54] COMBINATION OF CHOLECALCIFEROL DERIVATIVES FOR THE TREATMENT OF RENAL BONE DISEASE

[75] Inventors: Mordecai Popovtzer, Moshava Hayavaneet; Ben Z. Weiner, French Hill; Shmuel Edelstein, Rehovot; Zeev Mazor, French Hill; David Ladkani, Kiryat Yovel; Benjamin Shalita, Ramat Hagolan, all of Israel; John A. Kanis, Sheffield, England

[73] Assignee: Teva Pharmaceutical Industries Ltd., Israel

[21] Appl. No.: 76,459

[22] Filed: Jul. 22, 1987

[51] Int. Cl.$^5$ .............................................. A61K 31/59
[52] U.S. Cl. .................................... 514/170; 514/167; 514/168
[58] Field of Search ............................... 514/167, 170

[56] References Cited

U.S. PATENT DOCUMENTS

| | | | |
|---|---|---|---|
| 3,715,374 | 2/1973 | DeLuca | 260/397.2 |
| 4,340,604 | 7/1982 | Aoki et al. | 514/167 |
| 4,364,941 | 12/1982 | Kiyoki et al. | |
| 4,442,093 | 4/1984 | Maeda et al. | 514/167 |
| 4,590,184 | 5/1986 | Maeda et al. | 514/167 |
| 4,628,050 | 12/1986 | Maeda et al. | 514/167 |
| 4,866,047 | 11/1989 | Yamato et al. | 514/167 |

FOREIGN PATENT DOCUMENTS

| | | | |
|---|---|---|---|
| 2716601 | 4/1976 | Fed. Rep. of Germany | 514/167 |
| 2453650 | 7/1980 | France | |
| 2058564 | 4/1981 | United Kingdom | |

OTHER PUBLICATIONS

"Treatment of Hemodialysis Bone Disease with 24,25-(OH)$_2$D$_3$ and 1,25-(OH)$_2$D$_3$ Alone or in Combination" by Dunstan C. R., et al, *Mineral Electrolyte Metab.* 11:358-368(1985).

"Preliminary Trials with 24,25-Dihydroxyvitamin D$_3$ in Dialysis Osteomalacia", by Anthony B. Hodsman, et al; Mar. 1983, *The American Journal of Medicine*, vol. 74, #407.

"24,25(OH)$_2$D$_3$ Attenuates the Calcemic Effect of 1,25(OH)$_2$D$_3$ in Rats with Reduced Renal Mass" by D. Rubinger, et al, *Vitamin D.A. Chemical*, Biochemical and Clinical Update, 1985.

Garabedian M., et al, "The In Vitro Production and Activity of 24,25-Dihydroxycholecalciferol in Cartilage and Calvavium, " *Clinical Orthopedics and Related Research*, Dec. 1978, 241-248.

Statopolsky et al., *J. Clin. Invest.* 74, 2136 (1984).
Boyle et al, *J. Biol. Chem.*, 248, 4124 (1973).
Popovtzer et al, *Clin. Sci.*, 38, 297 (1970).
Popopovtzer, *Int. J. Artif. Org.*, 3, 1 (1980).
Abstract of Japanese application 5513920 by Teijin.
Kanis et al, "Comparative Physiology and Pharmacology of the Metabolites and Analogues of Vitamin D", Physicians Desk Reference, 40th Edition (1986).
Evans et al, Ibid., p. 302.
Pavlovitch et al, *J. Clin. Invest.* 68, 803 (1981).
Reeve et al, "Long-term Treatment of Osteoporosis with 24,25-Dihydroxycholecalciferol".
Endo et al, *Nature*, 286 (1980), 262-264.
Riis et al, "Vit. D-A Chemical Biochemical and Clinical Update", *Chemical Abstracts*, vol. 89 (1978), 89: 1977 1k.
Physicians' Desk Reference 40th Edition, 1986, p. 1810.
Pierides, Pharmacology and Therapeutic Use of Vitamin D and its Analogues, pp. 244-246.
Is 24,25-Dihydroxycholecalciferol a Calcium-Regulating Hormone in Man? J. A. Kanis, British Medical Journal, May 27, 1978, pp. 1382-1386.
English Language Abstract of EP No. 207,451, p. 64 of Other Organics, Hoff.
*Nature*, 30, Nov. 1978, pp. 517-519.
*Chem. Abstracts*, vol. 94, 1981, p. 78.
63-Pharmaceuticals, *Chem. Abstr.*, 103, 92850y 24,25-Dihydroxycholecalci. for Osteoporosis Therapy, p. 325.
B 5 Other Organics, p. 64, EP No. 207-451 A, "Syn.-vit.D/compsus.-contg. 1 alpha, 25,-dihydroxylated cholecalciferol cpds."
B 1 Steroids, p. 1, B FARMDOC, J6 1130-225-A, "Analgesic for Renal Osteodys, contains 24,25-di:hydroxy cholecalciferol".
*Proc. Nat. Acad. Sci., USA*, vol. 70, No. 8, pp. 2248-2252, Aug. 1973, "Biological Activity of 1α-Hydroxycholecal., A Synthetic Analog of the Hormonal Form of Vit. D$_3$", Haussler et al.
"1α-Hydroxy Derivative of Vit. D$_3$: A Highly Potent Analog of 1α,25-Dihydroxyvit D$_3$", *Science*, 180, pp. 190-191.
"Comparison of Effects of 1-Hydroxy-Vit. D$_3$ and 1,25-Dihydroxy-Vit., D$_3$ in Man", Brickman et al, *J. of Clin. Invest.*, 57, Jun. 1976, pp. 1540-1547.
Revue d'ensemble, "Le 24,25 dihydroxycholecalciferol a-t-il un rôle physiologique et physiopathologique? " Sebert et al, *Clinique medicale B et Service de Nephrologie*, Centre Hospitaller Universitiaire, Amiens, pp. 133-141, 1982.

(List continued on next page.)

[57] ABSTRACT

A method and composition for an improved treatment of human renal osteodystrophy, comprising the administration of 6-40 mcg/d (micrograms per day) of 24,25(OH)$_2$D$_3$ in combination with amounts of 1-alpha(OH)D$_3$ or 1,25(OH)$_2$D$_3$ or DHT$_2$, which will maintain in the serum of patients the calcium concentration at 10-11 mg/dl (milligrams per deciliter) and the phosphate concentration at 5.5-6.0 mg/dl (milligrams per deciliter) and the numerical multiplication product of calcium x phosphate not more than 60-65.

12 Claims, No Drawings

OTHER PUBLICATIONS

Serum Concentrations of 24,25-Dihydroxy Vitamin D in Different Degrees of Chronic Renal Failure, British Medical Journal, vol. 281, Sep. 13, 1980, pp. 712-713.

K. Galus et al, Effects of 1-Hydroxyvitamin $D_3$ and 24R,25-Dihydroxyvitamin $D_3$ on Bone Remodeling, Calcif. Tissue Int., 31, 209-213 (1980).

B. Lund et al, Treatment of Osteporosis of Ageing with 1α-Hydroxycholecalciferol, The Lancet, Dec. 13, 1975, pp. 1168-1171.

S. Lawoyin et al, Ability of 25-HydroxyVitamin $D_3$ Therapy to Augment Serum 1,25-and 24,25-Dihydroxy Vitamin D in Postmenopausal Osteoporosis, vol. 50, No. 3.

Goodwin et al, 24,25-Dihydroxyvitamin D is a Metabolite of Vitamin D Essential for Bone Formation, Nature, vol. 276, Nov. 30, 1978.

R. A. Donckerwolcke et al, Treatment of Renal Osteodystrophy in Children with Dihydrotachysterol and 24,25 Dihydroxyvitamin $D_3$, Clin. Nephrol., vol. 24, No. 6-1985, pp. 292-299.

Donald J. Sherrard et al, Use of 24,25 Dihydroxy Vitamin D ($OH_2D$), in Renal Osteodystrophy, Abstracts, Fifth Workshop on Vitamin D, Historic Williamsburg, Virginia, Feb. 14-19, 1982.

Jana Henriette Pavlovitch et al, Suppressive Effects of 24,25-Dihydroxycholecalciferol on Bone Resorption Induced by Acute Bilateral Nephrectomy in Rats, J. Clin. Invest., vol. 68, Sep. 1981, pp. 803-810.

B:5 Other Organics, p. 45, Week C50 (Article), Teijin KK, JA-045244.

*Primary Examiner*—Shep K. Rose
*Attorney, Agent, or Firm*—Sprung, Horn, Kramer & Woods

COMBINATION OF CHOLECALCIFEROL DERIVATIVES FOR THE TREATMENT OF RENAL BONE DISEASE

The invention relates to an improved method and pharmaceutical composition for the treatment of human bone diseases. More particularly the invention provides a method and composition for the treatment of renal osteodystrophy diseases in humans comprising the administration to a patient of 6–40 micrograms per day of 24,25 dihydroxycholecalciferol (hereafter "24,25(OH)$_2$D$_3$") in combination with 1-alpha-hydroxycholecalciferol (hereafter "1-alpha(OH)D$_3$") or 1,25-dihydroxycholecalciferol (hereafter "1,25(OH)$_2$D$_3$") or dihydrotachysterol (hereafter "DHT$_2$") in an amount per day which will maintain the patient's calcium serum concentration at 10–11 mg/dl and the phosphate concentration at 5.5–6.0 mg/dl.

As used herein, "d" means "day" and "dl" means "deciliter". Also "mcg" means "micrograms" and "mg" means "milligrams".

BACKGROUND OF THE INVENTION

Cholecalciferol (vitamin D$_3$) has been known to be intimately associated with bone metabolism and effectively used for the cure of rickets and osteomalacia since the early 1920s. Studies carried out during the last decade have shown that vitamin D$_3$ must be metabolically activated before functioning biochemically in its target tissues, including the intestine, bone and kidney. The dihydroxylated metabolite of vitamin D$_3$, namely 1,25(OH)$_2$D$_3$, was believed to be responsible for all the known biological functions of the vitamin. This compound is produced from cholecalciferol by C-25 hydroxylation in the liver followed by C-1 hydroxylation in the kidney. It was thus understandable why treatment with cholecalciferol was found to be ineffective in metabolic bone diseases, such as renal osteodystrophy, in patients who, owing to chronic kidney failure, are incapable of converting the cholecalciferol prohormone into its aforesaid dihydroxylated metabolite hormone.

The use of 1,25(OH)$_2$D$_3$ is now established in the treatment of renal bone diseases. Its administration increases calcium absorption from the gut and consequently, plasma calcium, and suppresses secondary hyperparathyroidism and its skeletal consequences. It also ameliorates osteomalacia in the presence of secondary hyperparathyroidism. The putative roles of 1,25(OH)$_2$D$_3$ in the bone are controversial and many of its actions can be accounted for by its effect to increase the ionized fraction of plasma calcium. This therapeutic effect is also the major cause of vitamin D toxicity, namely hypercalcemia. Its use is therefore contraindicated and indeed of limited value in patients with pre-existing hypercalcemia due to aluminum toxicity or tertiary hyperparathyroidism.

The failure of 1,25(OH)$_2$D$_3$ to control secondary hyperparathyroidism in many patients on dialysis stimulated the continuing search for more effective therapeutic means. Intravenous administration of 1,25(OH)$_2$D$_3$ has been recently reported to be more effective than the same drug administered by the oral route in suppressing secondary hyperparathyroidism (Slatopolsky et al., J. Clin. Invest 74, 2136, 1984). However, it has not solved the problem of secondary hyperparathyroidism in dialysis patients.

1-alpha(OH)D$_3$ is a synthetic analog of 1,25(OH)$_2$D$_3$. It is converted into the latter in the liver by 25-hydroxylation. 1-alpha(OH)D$_3$ is now also in clinical use for renal osteodystrophy, and its therapeutic effect is equivalent to that of 1,25(OH)$_2$D$_3$ apart from small differences in its biological half-life and dose response.

Although the treatment of chronic renal failure (CRF) with either 1,25(OH)$_2$D$_3$ or 1-alpha(OH)D$_3$ proved to be effective in maintaining normal concentrations of calcium and phosphate in the plasma, the beneficial results on the mineralization of bone matrix were highly incomplete and unsatisfactory.

There has been recent interest in other metabolites of vitamin D$_3$, notably 25(OH)D$_3$ and 24,25(OH)$_2$D$_3$ which may have different actions on target tissue than 1,25(OH)$_2$D$_3$ and 1-alpha(OH)D$_3$.

Until recently it was still controversial whether 24,25(OH)$_2$D$_3$ plays any physiological role in man and in animals, and whether it possesses a defined biological activity. In early observations this metabolite was considered to be only a by-product of renal 25(OH)D$_3$ metabolism. The uncertainty surrounding the physiological importance of 24,25(OH)$_2$D$_3$ stems partially from observations in animals.

In animal experiments, the effect of 24,25(OH)$_2$D$_3$ on stimulation of intestinal calcium absorption was contingent upon prior renal hydroxylation to 1,24,25(OH)$_3$D$_3$. Thus in nephrectomized animals 24,25(OH)$_2$D$_3$ failed to stimulate intestinal transport. Conversely in man where 24,25(OH)$_2$D$_3$ has been shown to be active in calcium metabolism 1,24,25(OH)$_3$D$_3$ was found to exert only a minimal effect. (Boyle et al., J. Biol. Chem. 248, 4174, 1973).

The increased calcium retention of 24,25(OH)$_2$D$_3$ is not associated with hypercalcemia, suggesting that 24,25(OH)$_2$D$_3$ may be directly or indirectly promoting calcium uptake in compartments other than the extracellular fluid. There is some evidence that skeletal retention of calcium is augmented. A number of experimental observations in animals suggest that both 1,25(OH)$_2$D$_3$ and 24,25(OH)$_2$D$_3$ are necessary for some aspects of skeletal metabolism. These include the normal differentiation of cartilage tissue, the healing of fractures and the mineralization of rachitic bone and cartilage and the prevention of parathyroid gland hyperplasia.

RENAL OSTEODYSTROPHY

Renal bone disease is a common complication in patients undergoing chronic dialysis.

Osteitis fibrosa cystica and osteomalacia are the two most common forms of uremic osteodystrophy. The typical histological features of osteitis fibrosa cystica are osteoclastic bone resorption forming cystic defects, endosteal and marrow space fibrosis with aggregates of osteoclasts and brown tumors. In addition there are morphological indications of rapid bone turnover reflected by increased active osteoid surface, increased formation of woven bone and enhanced tetracycline uptake. The characteristic roentgenographic features are subperiosteal bone resorption, cystic defects, frequently associated with osteosclerosis and extraskeletal calcifications. Secondary hyperparathyroidism that is responsible for osteitis fibrosa cystica, emerges early in the course of chronic renal disease. (Popovtzer et al., Clin. Sci. 38 297, 1970).

In chronic renal disease, loss of filtering units imposes increasing loads of phosphate on the remaining nephrons. The increased burden of phosphate may have several secondary consequences. The high phosphate in serum level causes a reciprocal fall in serum ionized calcium and the latter triggers secretion of parathyroid hormone (PTH). PTH restores both the serum phosphate and calcium to normal through its phosphaturic and calcemic actions. Subsequent reductions in nephron population will evoke a further rise in PTH leading to secondary hyperparathyroidism as an end-result (Popovtzer Inter. J. Artif. Org., 3, 1, 1980).

Reduced $1,25(OH)_2D_3$ activity, as demonstrated to be present in early renal disease, may cause secondary hyperparathyroidism by several mechanisms, (a) reduced intestinal absorption of calcium, (b) diminished skeletal calcemic response to PTH, and (c) loss of physiological suppression of PTH secretion.

Patients with renal bone diseases are often divided into two subgroups, an active bone disease subgroup and a non-active bone disease subgroup. This is done in accordance with the severity of the bone disease, particularly with regard to osteoclastic activity and bone forming activity, reflected by active osteoid and tetracycline uptake levels.

Often, in active bone disease, the osteoclast number equals or exceeds $0.3$ mm$^{-1}$ and the active bone resorption equals or exceeds 2.0%. Patients who do not meet these two criteria are included in the non-active bone disease subgroup.

DESCRIPTION OF PRIOR ART

Ornoy et al (Nature, 276, 517, 1978) demonstrated that the combined administration of 1-alpha(OH)D$_3$ with $24,25(OH)_2D_3$ produced a better cure of mineralization defect than 1-alpha(OH)D$_3$ alone in vitamin D deficient chicks. Galus et al (Calcif. Tissue Int., 31, 209, 1980) have shown that the administration of $24,25(OH)_2D_3$ in vitamin D-deficient dogs increases bone formation and mineralization and decreased bone resorption, while 1-alpha(OH)D$_3$ increased both mineralization and resorption. Pavlovitch et al (J. Clin. Invest., 68, 803, 1981) demonstrated an inhibition of increased bone resorption after acute bilateral nephrectomy by $24,25(OH)_2D_3$ in rats. In addition $24,25(OH)_2D_3$ blocked partially the stimulating effect of $1,25(OH)_2D_3$ on bone resorption. Rubinger et al (Proc. 6th Workshop Vit. D, Italy, 1985, p. 96) demonstrated that $24,25(OH)_2D_3$ suppressed the hypercalcemic effect of $1,25(OH)_2D_3$ in rats with chronic renal failure.

Tests in Human Patients

Kanis et al. (Brit. Med. J. 1382, 1978) suggested that $24,25(OH)_2D_3$ may be an important regulator of skeletal metabolism in man with potential value as a therapeutic agent in patients with chronic renal failure and osteoporosis.

Weisman et al (Brit. Med. J. 281, 712, 1980) indicated generally that treatment with both $1,25(OH)_2D_3$ and $24,25(OH)_2D_3$ may be needed to prevent and heal renal osteodystrophy.

In Japanese Patent Application No. 55 139-320, published on Oct. 31, 1980, combinations of $24,25(OH)_2D_3$ with either $1,25(OH)_2D_3$ or 1-alpha(OH)D$_3$ are claimed for the treatment of numerous bone and calcium metabolic diseases, amongst them also renal bone dystrophia. However, this patent application is very general and vague and fails to disclose how to use these combinations in any of the diseases mentioned, including renal osteodystrophy.

Dunstan et al. (Mineral Electrolyte Metab. 11, 358, 1985) concluded that "$1,25(OH)_2D_3$ is a useful agent in the treatment of renal bone diseases but no therapeutic value is consecture for $24,25(OH)_2D_3$".

Thus, the above publication teaches away from a combination of $24,25(OH)_2D_3$ with $1,25(OH)_2D_3$ and consequently also with 1-alpha(OH)D$_3$ which is biochemically and therapeutically equivalent to $1,25(OH)_2D_3$.

SUMMARY OF INVENTION

The invention provides a novel method and pharmaceutical composition for the improved treatment of human renal osteodystrophy patients undergoing hemodialysis.

According to one aspect of the invention, the new method comprises the administration to such a patient 6–40 mcg/d of $24,25(OH)_2D_3$ in combination with daily amounts of 1-alpha(OH)D$_3$ or $1,25(OH)_2D_3$ or DHT$_2$ which will suffice to maintain normal calcium levels, namely at 10–11 mg/dl, and the phosphate concentration at 5.5–6.0 mg/dl, and that the numerical value of the multiplication of the calcium and the phosphate concentrations in the serum should be about 60–65.

The ingredients in the combination may be administered separately, all of them orally by means of capsules or, if preferred, 1-alpha(OH)D$_3$ and $1,25(OH)_2D_3$ parenterally.

The preferred method of administration is orally by means of capsules containing 5 mcg of $24,25(OH)_2D_3$ and various amounts of 1-alpha(OH)D$_3$ or $1,25(OH)_2D_3$ such as 0.25 mcg, 0.5 mcg, 0.75 mcg and 1.0 mcg per capsule.

The new method of treatment of chronic renal failure (CRF) patients by means of the specific combinations of $24,25(OH)_2D_3$ with 1-alpha(OH)D$_3$ or $1,25(OH)_2D_3$ in the relative amounts of each components as stated above offers significant improvements in the clinical symptoms, in the various bone histological parameters and blood biochemistry of these patients.

Another aspect of the invention is the use of the novel combination of $24,25(OH)_2D_3$ with 1-alpha(OH)D$_3$ or $1,25(OH)_2D_3$ in the stated relative proportions for CRF patients simultaneously with other drugs which may be used in their treatment. In addition dihydrotachysterol (DHT$_2$), which has been shown to be effective in combination with $24,25(OH)_2D_3$ in the treatment of renal osteodystrophy in adults and children can be used in combination with $24,25(OH)_2D_3$ (van Diemen-Steenvoorde, et al., Clin. Nephrol., 24, 292, 1985).

DETAILED DESCRIPTION OF INVENTION

The clinical treatment at present in practice for patients with renal bone diseases, including those undergoing hemodialysis, comprises the administration of either $1,25(OH)_2D_3$ or 1-alpha(OH)D$_3$ or DHT$_2$ orally or parenterally.

Although these cholecalciferol analogs proved to be effective in maintaining normal concentrations of calcium and phosphate in the plasma of the patients, they showed little beneficial results on the bone mineralization of the bone matrix. The treatment consequently failed to improve clinical bone symptoms and bone histological parameters of the patients suffering from osteitis fibrosa cystica resulting from secondary hyperparathyroidism and from osteomalacia. Although some Prior Art publications indicated that both $1,25(OH)_2D_3$ and $24,25(OH)_2D_3$ may be necessary for skeletal metabolism and bone formation and mineralization, and other publications suggested that the combined treatment of the above two cholecalciferol metabolites in renal osteodystrophy may have some therapeutic advantages, there was no disclosure in the Prior Art of how to perform or use such a combination which will result in any advantageous therapeutic effects.

By virtue of the present invention there was discovered a specific method and pharmaceutical combination of $24,25(OH)_2D_3$ with either 1-alpha$(OH)D_3$, $1,25(OH)_2D_3$ or $DHT_2$ which will offer considerable therapeutic advantages to renal osteodystrophy patients (also called chronic renal failure - CRF - patients).

Studies have been provided where the patients were randomly allocated into two groups. One group of patients was treated with 1-alpha$(OH)D_3$ alone or $1,25(OH)_2D_3$ alone (hereafter the "control group") in daily dosages to maintain normal serum concentrations of calcium and phosphate. To the second group of patients (hereafter the "treatment group") was administered $24,25(OH)_2D_3$ in daily dosages ranging from 10 mcg to 40 mcg in combination with 1-alpha$(OH)D_3$ or $1,25(OH)_2D_3$ in daily amounts which would maintain the patients calcium (Ca) serum concentrations at 10–11 mg/dl and phosphate (P) serum concentration at 5.5–6.0 mg/dl, and the Ca×P numerical product should not exceed 60–65.

The daily dosages of 1-alpha$(OH)D_3$ or $1,25(OH)_2D_3$ in both the "treatment group" and in the "control group" were adjusted for every patient individually, in order to maintain the serum concentrations of calcium and phosphate at the normal range levels as stated above.

The actual daily doses of 1-alpha$(OH)D_3$ or $1,25(OH)_2D_3$ administered to the patients ranged from 0.25 mcg to 3.0 mcg.

The controlled studies have surprisingly shown that significant therapeutic improvements were achieved in the treatment group in comparison with the control group. Improvements were observed in both aspects of the renal bone disease, in the bone histological parameters as well as in the relief of the bone clinical symptoms.

Bone Histomorphometry

Two bone biopsies were obtained from the iliac crest, one at the outset of the study and the other upon its completion. The histomorphometry of the biopsies showed the following favorable results:

The trabecular bone volume in the treatment group was considerably lower than in the control group.

The active osteoid surface was significantly reduced in the treatment group compared to the control group. This was shown in the second biopsy, especially in patients with relatively high active osteoid surface levels in the first biopsy.

In the resorption surface, a statistically significant decrease was observed in the treatment group, whereas no change could be detected in the control group.

The improvements in the bone resorption were even more pronounced in the active bone disease subgroup, which was defined as having an osteoclast number equal to or exceeding 0.3 $mm^{-1}$ and active bone resorption equal to or exceeding 2.0%. All patients with active bone disease in the treatment group showed a significant decrease in bone resorption, whereas in the control group there was no change or even an increase in bone resorption.

Clinical symptoms

With respect to clinical manifestations before and after treatment in the active bone disease subgroup, such as bone pains and tenderness, muscle pains and pruritus, there was a significant improvement in the clinical symptoms in the treatment group. In the control group, the clinical symptoms remained unchanged, or even worsened.

Untoward Side Effects

Careful observation in all studies have not revealed untoward side effects in the treatment group that could be attributed to $24,25(OH)_2D_3$ given orally at a daily dose of either 10 mcg or 40 mcg over the whole period of the studies. Thus $24,25(OH)_2D_3$ can be considered a "very safe drug" when administered at the abovementioned daily dosage. In addition, it was found that $24,25(OH)_2D_3$ administered in combination with 1-alpha-hydroxylated $D_3$ derivatives increased the patient's tolerance of these derivatives and reduced the risk of hypercalcemia.

The best mode of carrying out the invention

The clinical trials and studies of the present invention indicate that the best mode of carrying out the invention is as follows:

The treatment of patients with renal osteodystrophy, including those undergoing chronic hemodialysis, should comprise the administration to each patient of 10 mcg per day of $24,25(OH)_2D_3$ in combination with either 1-alpha$(OH)D_3$, $1,25(OH)_2D_3$ or $DHT_2$ in daily doses which will maintain the patient's calcium concentration at the upper normal levels of 10 to 11 mg/dl and the phosphate serum concentration at 5.5–6.0 mg/dl. Another criterion for the daily dosage of 1-alpha$(OH)D_3$, $1,25(OH)_2D_3$ or $DHT_2$ should be that the numerical value of the multiplication "calcium × phosphate" should not exceed 60–65 during the treatment.

With the specific combination of 10 mcg per day of $24,25(OH)_2D_3$ and the appropriate amounts of 1-alpha$(OH)D_3$, $1,25(OH)_2D_3$ or $DHT_2$, the most favorable therapeutic effects were obtained in the treatment of renal osteodystrophy patients considering all the aspects of the disease: The blood biochemical and hematological measurements, the bone histomorphometry and the clinical manifestations. These favorable results are outlined in detail in example 7 (Study I).

The rationale for the administration of 10 mcg of $24,25(OH)_2D_3$ per day to patients can be based on calculations obtained from the physiological and therapeutic experiments conducted in the chick. The optimal physiological dose of $24,25(OH)_2D_3$ in the chick was found to be 0.3 mcg, which is about 3 times that of $1,25(OH)_2D_3$ or 1-alpha$(OH)D_3$. As the therapeutic daily doses of the latter in the human are 20 times the physiological doses, the daily therapeutic dose of $24,25(OH)_2D_3$ in the human should be at least $20 \times 0.3$ mcg, namely 6 mcg.

The best daily dose of $24,25(OH)_2D_3$ in CRF patients was found by the present invention to be 10 mcg which is only in slight excess of the theoretical dose of 6.0 mcg/d.

$24,25(OH)_2D_3$ should best be administered by means of 2 soft gelatine capsules per day, containing 5 mcg per capsule, one in the morning and one in the evening.

Even more preferable is the administration by means of soft gelatine capsules containing a combination of 5 mcg 24,25(OH)$_2$D$_3$ and amounts of 0.25 or 1.0 mcg of 1-alpha(OH)$_2$D$_3$ or 1,25(OH)$_2$D$_3$ in accordance with the needs of each individual patient.

In the case where 1-alpha(OH)D$_3$ or 1,25(OH)$_2$D$_3$ is administered separately from 24,25(OH)$_2$D$_3$ it can be done orally by means of soft gelatine capsules or tablets containing 0.25 mcg or 1.0 mcg of the active ingredient. Alternatively, it can also be administered parenterally by means of ampoules containing the desired amounts of the active ingredient and stabilized by means of sodium ascorbate and a buffer to pH of 6.4 to 7.8 (See U.S. Pat. No. 4,308,264).

The soft gelatine capsules of all the active ingredients (1-alpha(OH)D$_3$, 1,25(OH)$_2$D$_3$ or 24,25(OH)$_2$D$_3$) may be prepared in arachis oil, propylene glycol, glycerin and other suitable solvents together with a stabilizer and a preservative.

Another embodiment of the invention is the use of the combination of 24,25(OH)$_2$D$_3$ in the range given with dihydrotachysterol (DHT$_2$), which is usually administered orally by means of tablets, capsules, or solutions.

The beneficial effect of the simultaneous administration of 24,25(OH)$_2$D$_3$ and DHT$_2$ was demonstrated by an uncontrolled study in patients with dialysis related osteomalacia. (Hodsman, et al., Am. J. Med. 74, 407, 1983). A more recent study showed also the benefits of this combination in children undergoing chronic dialysis with hyperparathyroid bone diseases, resulting in a significant decrease in the number of osteoblasts. (van Diemen-Steenvoorde, et al., Clin. Nephrol., 24, 292, 1985).

The combination of the invention given simultaneously with DHT$_2$ is expected to give even more favorable results in cases of osteomalacia and renal bone disease of secondary hyperparathyroidism.

Assumed Mode of Action of The Invention

In vitro studies have demonstrated the effective anabolic action of 24,25(OH)$_2$D$_3$ in the presence of 1,25(OH)$_2$D$_3$ and PTH. Only combined treatment of 1,25(OH)$_2$D$_3$, 24,25(OH)$_2$D$_3$ and PTH will induce a significant increase in bone mineral deposition in cultured bones in vitro. Each one of the components operates on a different cellular function related to bone formation, and jointly they have synergistic effect on bone.

It is well known from the literature that, while both 1,25(OH)$_2$D$_3$ and 24,25(OH)$_2$D$_3$ are similar in stimulating calcium absorption at the intestinal mucosal level, they differ in the nature of their action on the bone level in renal osteodystrophy patients.

While 1,25(OH)$_2$D$_3$ in physiological doses directly stimulates bone resorption, 24,25(OH)$_2$D$_3$ exerts an opposite action on the bone level. Thus, the advantage of simultaneous administration of both metabolites in the proportions of the invention to renal osteodystrophy patients is in the ability of 24,25(OH)$_2$D$_3$ to offset the effects of 1,25(OH)$_2$D$_3$ (or its analogs 1-alpha(OH)D$_3$ and DHT$_2$) with regard to the resorbing action on the bone, but on the other hand a synergistic action with respect to gut absorption, bone mineralization, and less likely, parathyroid hormone (PTH) suppression.

The following examples provide an illustration of the invention, but should not be construed as to limit the scope of the invention.

EXAMPLE 1

Soft Gelatine Capsules of 1-alpha(OH)D$_3$

Each 0.25 mcg capsule contains:

| | |
|---|---|
| 1-alpha-HYDROXYCHOLECALCIFEROL | 0.275 mcg* |
| CITRIC ACID anhydrous | 0.015 mg |
| PROPYL GALLATE | 0.020 mg |
| VITAMIN E (dl-alpha TOCOPHEROL) | 0.020 mg |
| ALCOHOL dehydrated | 1.145 mg |
| PEANUT OIL (ARACHIS OIL) | 98.800 mg |
| Total fill weight per capsule: | 100.0 mg |

*Includes 10 percent excess.

EXAMPLE 2

Soft Gelatine Capsules of 1.0 mcg 1-alpha(OH)D$_3$

Each 1.0 mcg capsule contains:

| | |
|---|---|
| 1-alpha-HYDROXYCHOLECALCIFEROL | 1.100 mcg* |
| CITRIC ACID anhydrous | 0.015 mg |
| PROPYL GALLATE | 0.020 mg |
| VITAMIN E (dl-alpha TOCOPHEROL) | 0.020 mg |
| ALCOHOL dehydrated | 1.145 mg |
| PEANUT OIL (ARACHIS OIL) | 98.800 mg |
| Total fill weight per capsule: | 100.0 mg |

*Includes 10 percent excess.

EXAMPLE 3

Soft Gelatine Capsules of 0.25 mcg 1,25(OH)$_2$D$_3$

Each 0.25 mcg capsule contains:

| | |
|---|---|
| 1,25-HYDROXYCHOLECALCIFEROL | 0.275 mcg* |
| CITRIC ACID anhydrous | 0.015 mg |
| PROPYL GALLATE | 0.020 mg |
| VITAMIN E (dl-alpha TOCOPHEROL) | 0.020 mg |
| ALCOHOL dehydrated | 1.145 mg |
| PEANUT OIL (ARACHIS OIL) | 98.800 mg |
| Total fill weight per capsule: | 100.0 mg |

*Includes 10 percent excess.

EXAMPLE 4

Soft Gelatine Capsules of 1.0 mcg of 1,25(OH)$_2$D$_3$

Each 1.0 mcg capsule contains:

| | |
|---|---|
| 1,25-DIHYDROXYCHOLECALCIFEROL | 1.100 mcg* |
| CITRIC ACID anhydrous | 0.015 mg |
| PROPYL GALLATE | 0.020 mg |
| VITAMIN E (dl-alpha TOCOPHEROL) | 0.020 mg |
| ALCOHOL dehydrated | 1.145 mg |
| PEANUT OIL (ARACHIS OIL) | 98.800 mg |
| Total fill weight per capsule: | 100.0 mg |

*Includes 10 percent excess.

EXAMPLE 5

Soft Gelatine Capsules of 5.0 mcg of 24,25(OH)$_2$D$_3$

Each 5.0 mcg capsule contains:

| | |
|---|---|
| 24R,25-DIHYDROXYCHOLECALCIFEROL | 5.500 mcg* |
| CITRIC ACID anhydrous | 0.015 mg |
| PROPYL GALLATE | 0.020 mg |
| VITAMIN E (dl-alpha TOCOPHEROL) | 0.020 mg |
| ALCOHOL dehydrated | 1.145 mg |
| PEANUT OIL (ARACHIS OIL) | 98.800 mg |

| | |
|---|---|
| -continued | |
| Total fill weight per capsule: | 100.0 mg |

*Includes 10 percent excess.

EXAMPLE 6

Soft Gelatine Capsules of 10.0 mcg of $24,25(OH)_2D_3$

Each 10.0 mcg capsule contains:

| | |
|---|---|
| 24R,25-DIHYDROXYCHOLECALCIFEROL | 11.000 mcg* |
| CITRIC ACID anhydrous | 0.015 mg |
| PROPYL GALLATE | 0.020 mg |
| VITAMIN E (dl-alpha TOCOPHEROL) | 0.020 mg |
| ALCOHOL dehydrated | 1.145 mg |
| PEANUT OIL (ARACHIS OIL) | 98.800 mg |
| Total fill weight per capsule: | 100.0 mg |

*Includes 10 percent excess.

EXAMPLE 7

Soft Gelatine Capsules containing combination of 0.25 mcg or 1.0 mcg of 1-alpha$(OH)D_3$ plus 5 mcg of $24,25(OH)_2D_3$ Each 1.0 mcg capsule contains:

| | |
|---|---|
| 1-alpha-HYDROXYCHOLECALCIFEROL | 1.100 mcg* |
| 24R,25-DIHYDROXYCHOLECALCIFEROL | 5.500 mcg* |
| CITRIC ACID anhydrous | 0.015 mg |
| PROPYL GALLATE | 0.020 mg |
| VITAMIN E (dl-alpha TOCOPHEROL) | 0.020 mg |
| ALCOHOL dehydrated | 1.145 mg |
| PEANUT OIL (ARACHIS OIL) | 98.800 mg |
| Total fill weight per capsule: | 100.0 mg |

*Includes 10 percent excess.

EXAMPLE 8

Soft Gelatine Capsules containing combination of 0.25 mcg or 1.0 mcg of $1,25(OH)_2D_3$ plus 5 mcg of $24,25(OH)_2D_3$ Each 1.0 mcg capsule contains:

| | |
|---|---|
| 1,25-DIHYDROXYCHOLECALCIFEROL | 1.100 mcg* |
| 24R,25-DIHYDROXYCHOLECALCIFEROL | 5.500 mcg* |
| CITRIC ACID anhydrous | 0.015 mg |
| PROPYL GALLATE | 0.020 mg |
| VITAMIN E (dl-alpha TOCOPHEROL) | 0.020 mg |
| ALCOHOL dehydrated | 1.145 mg |
| PEANUT OIL (ARACHIS OIL) | 98.800 mg |
| Total fill weight per capsule: | 100.0 mg |

*Includes 10 percent excess.

EXAMPLE 9

Treatment of Chronic Renal Failure (CRF) patients with a combination of $24,25(OH)_2D_3$ and 1-alpha$(OH)D_3$ (Study I).

The study included 56 CRF male and female adult patients undergoing chronic hemodialysis at several medical centers. The patients were randomly allocated into two groups, one group of 31 patients was treated with a combination of $24,25(OH)_2D_3$ and 1-alpha$(OH)D_3$ (the "treatment group") and the other group of patients was treated with 1-alpha$(OH)D_3$ along (the "control group").

Patients of both groups were administered 1-alpha$(OH)D_3$ in capsules of 0.25 mcg or 1.0 mcg per capsule. The dose was adjusted for every patient individually so as to maintain the serum calcium at the upper normal level, but not higher than 11 mg/dl, and the phosphate level not higher than 6.0 mg/dl or that the numerical multiplication product of calcium × phosphate did not exceed 65. The actual daily doses of 1-alpha$(OH)D_3$ ranged from 0.25 mcg to 3.0 mcg.

The treatment group was administered in addition to 1-alpha$(OH)D_3$ also $24,25(OH)_2D_3$ at a daily dose of 10 mcg by means of 2 capsules containing 5 mcg per capsule, one in the morning and the other in the evening.

The dose of 10 mcg of $24,25(OH)_2D_3$ was constant throughout the study which lasted 10–16 months.

Three major categories of variables were measured and monitored during the treatment. These were: (1) blood biochemistry, (2) bone histomorphometry (static and dynamic), and (3) clinical follow-up.

Blood Biochemistry

As stated before, special attention was given to the blood levels of calcium, phosphate and to the multiplication product of calcium × phosphate.

The serum calcium concentration was found to be significantly higher in the treated group during the period 3–8 months of the study, in comparison with the control group though the levels remained within the normal range.

An increase in the $24,25(OH)_2D_3$ serum levels in the treated groups was the only significant change between the two groups during the whole study.

Bone histomorphometry

One bone biopsy was taken from all patients under local anesthesia applied to both plates of the iliac crest at the onset of the study, and a second biopsy was obtained in a similar fashion from the contralateral side of the iliac crest approximately one year later, upon the completion of the study.

The results obtained from the biopsies showed statistically significant changes between the control group and the treatment group. These were as follows:

trabecular bone volume. This measurement increased significantly during treatment in the control group only. At the end of the study it was much lower in the treatment group compared to the control group.

active osteoid surface. The relatively high active osteoid surface levels shown by some patients at the first biopsy were significantly lower at the second biopsy only in the treatment group and not in the control group.

resorption surface. Generally, a statistically significant decrease in the resorption surface was shown only in the treatment group. There was no significant change in the control group. At the end of the study, the resorption surface in the treatment group was significantly lower than that in the control group.

Even more pronounced differences in the histomorphological results were shown in those patients in whom the respective parameters exhibited high levels at the initial biopsy, namely in patients with a a more severe bone disease.

In view of this observation the patients in the study were subdivided into two types of bone disease, an active bone disease subgroup and a non-active bone disease subgroup. The division was made according to the osteoclast number and the active resorption surface.

Patients with an osteoclast number equal to or exceeding 2.0% were included in the active bone disease subgroup, and those with lower values were included in the non-active bone disease subgroup.

The results of this study show that all CRF patients with active bone disease in the treatment group showed a most significant decrease in active resorption surface, whereas patients with active bone disease in the control group either showed no change or even an increase in this parameter.

However, also in the non-active bone disease subgroup 11 out of 12 patients who were treated with the combination showed a significant reduction in the active resorption surface; in contrast, the control group showed no reduction.

Clinical follow-up. With respect to clinical manifestations of the disease of the treated patients, such as bone pains and tenderness, muscle pains, pruritus and others, there was generally a marked improvement only in the treatment group. This improvement was especially marked in the treatment active bone disease subgroup where most patients became asymptomatic. No relief of these clinical symptoms was observed in the control group.

No untoward side effects could be detected in the patients treated with the combination which could be attributed to $24,25(OH)_2D_3$ administered orally at a daily dose of 10 mcg.

This study thus demonstrates that the administration of $24,25(OH)_2D_3$ to renal osteodystrophy patients in daily doses of 10 mcg in combination with 1-alpha(OH)$D_3$ in doses sufficient to maintain the levels of calcium and phosphate in the upper normal range, results in marked improvements in the bone parameters as well as in clinical manifestations, in comparison with the control group which was treated with 1-alpha(OH)$D_3$ alone in similar doses.

EXAMPLE 10

Treatment of CRF patients with a combination of $24,25(OH)_2D_3$ and 1-alpha(OH)$D_3$ (Study II)

The study included 62 CRF male and female adult patients undergoing chronic hemodialysis and lasted for 10–22 months. As in Study I, the CRF patients were randomly allocated into two groups: 34 patients were allocated to the combination treatment of $24,25(OH)_2D_3$ and 1-alpha(OH)$D_3$. In this study the daily dose of $24,25(OH)_2D_3$ was 40 mcg and that of 1-alpha(OH)$D_3$ was sufficient to maintain the concentration of calcium and phosphate in the serum at the upper normal level in a manner as stated in Study I.

The patients in the control group received 1-alpha(OH)$D_3$ alone in similar doses as in Study I.

The blood chemistry results were similar to those obtained in Study I.

The bone histomorphometric measurements performed in 50 patients (25 in each group) showed that the combination treatment resulted in the following favorable results:

(1) a decrease in the trabecular bone volume
(2) a decrease in the resorption surface
(3) a slight decrease in the active resorption surface
(4) a slight decrease in osteoclast number and
(5) a slight decrease in fibrotic surface.

These improvements in the bone parameters were not as significant as in Study I. The improvements in the clinical symptoms were also not as prominent in the treatment group in comparison with the control group as was observed in Study I.

EXAMPLE 11

Combined treatment of CRF patients with $24,25(OH)_2D_3$ and $1,25(OH)_2D_3$ (Study III)

The study included 62 CRF patients with bone diseases, such as osteitis fibrosa cystica and osteomalacia. The patients were randomly allocated into three groups:

(1) The control group A which included 25 patients who were treated with $24,25(OH)_2D_3$ alone at doses of 20 mcg/d.
(2) The control group B which included 24 patients who were treated with $1,25(OH)_2D_3$ alone at varying daily doses ranging from 0.25 mcg to 2.0 mcg so as to maintain the concentration of calcium and phosphate at the upper normal range as in Study I.
(3) The treatment group which included 13 patients. These patients were administered a combination of $24,25(OH)_2D_3$ at 20 mcg/d and $1,25(OH)_2D_3$ at daily doses similar to those administered to patients in control group B.

The study showed the following results:

The combined treatment induced a less marked increment in serum calcium than that observed in the control group treated with $1,25(OH)_2D_3$ alone.

However, the decrement in alkaline phosphatase activity in the treatment group appeared to be less marked than in patients given $1,25(OH)_2D_3$ alone.

The following conclusions may be drawn from the study:

(1) The addition of $24,25(OH)_2D_3$ with $1,25(OH)_2D_3$ for the treatment of renal bone disease does not aggravate hypercalcemia, nor does it impair the apparent effectiveness of $1,25(OH)_2D_3$ in the treatment of hyperparathyroid bone disease.
(2) The combination of $1,25(OH)_2D_3$ and $24,25(OH)_2D_3$ in the treatment of hyperparathyroid bone disease is of value in those patients who had previously been shown to be refractory to treatment with $1,25(OH)_2D_3$ alone.

What is claimed is:

1. A method for the treatment of osteitis fibrosa cystica disease in human patients comprising administering to said patients a combination of 3 to 5 micrograms of 24,25-dihydroxycholecalciferol and 0.25 to 1.0 microgram of 1-alpha-hydroxycholecalciferol or of 0.5 to 1.0 milligram of dihydrotachysterol, wherein the combination is administered per day as follows: 6–40 micrograms per day of 24,25-dihydroxycholecalciferol in combination with a compound selected from the group consisting of 1-alpha-hydroxycholecalciferol and dihydrotachysterol, in an amount per day which will maintain the patient's calcium serum concentration at about 10 to 11 mg/dl and phosphate serum concentration at about 5.5 to 6.0 mg/dl.

2. A method according to claim 1 wherein said combination comprises 5 micrograms of 24,25-dihydroxycholecalciferol.

3. A method according to claim 1, wherein said combination comprises a medicament in dosage unit form, said combination in a mixture with an inert pharmaceutical carrier, said mixture in the form of tablets, pills, dragees, capsules, ampoules or suppositories.

4. A method of claim 3, wherein the mixture is in the form of a soft gelatin capsule.

5. A method according to claim 1, wherein the combination further comprises a stabilizing agent comprising Vitamin E, citric acid, propyl gallate and arachis oil.

6. The method of claim 1 in which the numerical value of the serum calcium concentration multiplied by the numerical value of the serum phosphate concentration results in a numerical product of about 60 to about 65.

7. A method of claim 1 wherein the 24,25-dihydroxycholecalciferol is administered in an amount of 10–40 mcg/d.

8. A method of claim 1 wherein the 24,25-dihydroxycholecalciferol is administered in an amount of 10 mcg/d.

9. A method according to claim 1, wherein the combination is administered twice a day.

10. A method according to claim 1, wherein the composition further comprises PTH.

11. A method according to claim 1, wherein the combination consists essentially of 24,25-dihydroxycholecalciferol and dihydrotachysterol.

12. A method according to claim 1, wherein the combination consists essentially of 24,25-dihydroxycholecalciferol and 1-alpha-hydroxycholecalciferol.

* * * * *